United States Patent [19]
Ouchi

[11] Patent Number: 6,093,195
[45] Date of Patent: Jul. 25, 2000

[54] ENDOSCOPIC TREATMENT TOOL

[75] Inventor: Teruo Ouchi, Saitama, Japan

[73] Assignee: Asahi Kogaku Kogyo Kabushiki Kaisha, Tokyo, Japan

[21] Appl. No.: 09/369,355

[22] Filed: Aug. 6, 1999

[30] Foreign Application Priority Data

Aug. 17, 1998 [JP] Japan .................................. 10-230372

[51] Int. Cl.⁷ .................................................. A61B 17/24
[52] U.S. Cl. ............................. 606/113; 604/22; 606/114
[58] Field of Search .................................... 606/110, 113, 606/114, 170, 79; 604/22

[56] References Cited

U.S. PATENT DOCUMENTS

| | | | |
|---|---|---|---|
| 5,735,289 | 4/1998 | Pfeffer et al. | 606/113 |
| 5,746,747 | 5/1998 | McKeating | 606/114 |
| 5,906,621 | 5/1999 | Secrest et al. | 606/114 |
| 6,007,546 | 12/1999 | Snow et al. | 606/113 |

*Primary Examiner*—Gene Mancene
*Assistant Examiner*—Eduardo C. Robert
*Attorney, Agent, or Firm*—Greenblum & Bernstein, P.L.C.

[57] ABSTRACT

An endoscopic treatment tool including a flexible sheath (1) that is to be passed into or out of a treatment tool insertion channel in an endoscope and which has openings (4A, 4B) formed at and near the distal end to communicate with the interior of the flexible sheath (1). A plurality of manipulating wires (3A, 3B) that have treating members (5A, 5B) are coupled to the distal ends and are passed through the flexible sheath (1) such that they can be moved back and forth independently of each other along the longitudinal axis. The treating member (5a) is provided to have access to the flexible sheath (1) via the opening (4A) at its distal end and the other treating member (5B) is provided to have access to the flexible sheath (1) via the opening (4b) near its distal end.

17 Claims, 17 Drawing Sheets

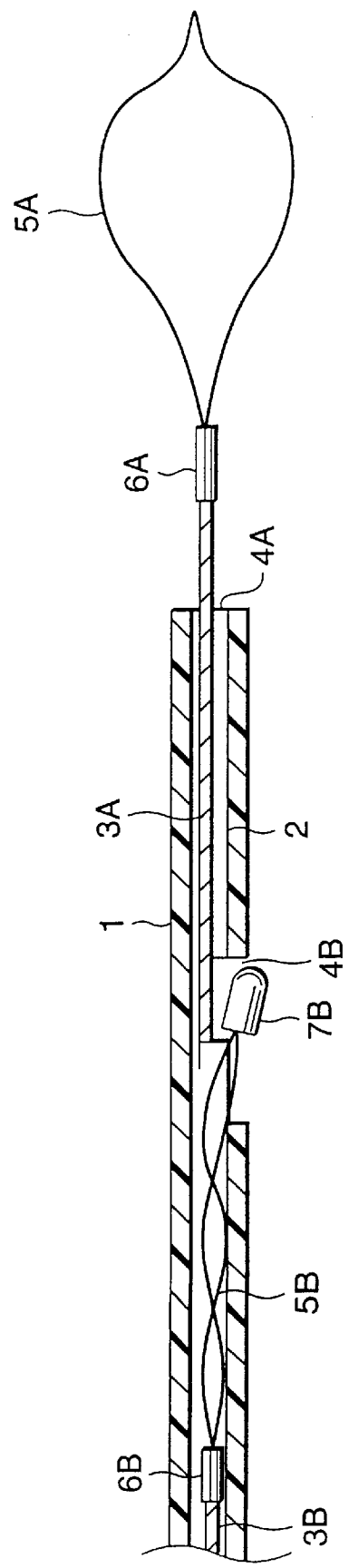

ENDOSCOPIC TREATMENT TOOL

BACKGROUND OF THE INVENTION

The present invention relates to an endoscopic treatment tool which is passed into or out of a treatment tool insertion channel in an endoscope in order to remove and retrieve polyps in body cavities and perform other treatments.

Endoscopic treatment tools are generally comprised of a flexible sheath that is to be passed into or out of a treatment tool insertion channel in an endoscope, a manipulating wire that is passed through the flexible sheath in such a manner that it can be moved back and forth along the longitudinal axis thereof, and a treating member that is coupled to the distal end of the manipulating wire and which is allowed to eject from or retracted into the distal end of the flexible sheath by remote control from the proximal end.

If a plurality of polyps are found in a body cavity, a high-frequency snare is first inserted into an endoscope and one polyp is removed with it, which is then slipped out of the endoscope, leaving the polyp in the body cavity; thereafter, a foreign matter collecting tool is inserted into the endoscope and the removed polyp is scooped with the tool and taken out of the body cavity before another polyp is removed with the snare. However, it is cumbersome to alternate the high-frequency snare with the foreign matter collecting tool in the steps of insertion into an endoscope and removal from it. With a view to eliminating this problem, it has been proposed in U.S. Pat. No. 5,741,271 that a plurality of treating members including a high-frequency snare loop and a foreign matter retaining or capturing basket should be provided at the distal end of a single flexible sheath so that polyps can be both removed and collected with a single treatment tool.

The prior art endoscopic treatment tool disclosed in U.S. Pat. No. 5,741,271 is so designed that both the high-frequency snare loop and the foreign matter retaining basket are protruded from and retracted into the flexible sheath via an opening provided at the distal end of the flexible sheath. If a polyp removed with the high-frequency snare loop is retained in the basket, the basket will interfere with the high-frequency snare loop, making it impossible to remove another polyp.

To remove the next polyp, the treatment tool must first be slipped out of the endoscope, the already removed polyp is taken out of the basket and the treatment tool is reinserted into the endoscope. This procedure is no less cumbersome than in the case of using a plurality of treatment tools.

SUMMARY OF THE INVENTION

An object, therefore, of the present invention is to provide an endoscopic treatment tool that is capable of repeating a plurality of treatments including the removal and retrieval of polyps without being withdrawn from an endoscope.

The stated object of the invention can be attained by an endoscopic treatment tool having a flexible sheath that is to be passed into or out of a treatment tool insertion channel in an endoscope and which has openings formed respectively at and near the distal end to communicate with the interior of said flexible sheath. At least two manipulating wires are provided, which have treating members coupled to the distal ends of said at least two manipulating wires, respectively, and which are passed through said flexible sheath such that they can be moved back and forth along the longitudinal axis independently of each other. One of said treating members is provided to have access to said flexible sheath via said opening at its distal end and the other of said treating members is provided to have access to said flexible sheath via said opening near its distal end.

The treating member which has access to said flexible sheath via the opening at its distal end may be a high-frequency snare loop and the treating member which has access to said flexible sheath via the opening near said distal end may be a foreign matter retaining member. Alternatively, the treating member which has access to said flexible sheath via the opening at its distal end may be a foreign matter retaining member and the treating member which has access to said flexible sheath via the opening near said distal end may be a high-frequency snare loop.

If desired, at least two passages through which said at least two manipulating wires are respectively passed independently of each other are formed through said flexible sheath along the longitudinal axis. In this case, the endoscopic treatment tool may be adapted such that a passage communicating with said opening near the distal end of said flexible sheath is absent in that portion of said flexible sheath which is more distal than said opening so that the outer shape of that portion of the flexible sheath is sized to be thinner by an amount corresponding to the elimination of the passage.

If desired, said opening near the distal end of said flexible sheath may be formed in the sidewall of said flexible sheath. In this case, the endoscopic treatment tool may have a soft filling provided in that portion of the passage communicating with said opening near the distal end which is more distal than said opening. In this case, said filling may form a slope by which the inner surface of that portion of said passage which is closer to the basal end than said opening near the distal end is connected smoothly to said opening.

If desired, said at least two manipulating wires may be collectively passed through a single passage formed through said flexible sheath along the longitudinal axis. In this case, at least one of said at least two manipulating wires may be provided with an electrically insulating coat.

In yet another embodiment, a fluid passage may be formed through said flexible sheath along the longitudinal axis separately from the passage or passages through which said at least two manipulating wires are to be passed. If desired, the endoscopic treatment tool may be adapted to have a tip provided at the distal end of the treating member that has access to said flexible sheath via the opening near its distal end, said tip being of such a shape and a size that it is incapable of passing through said opening near the distal end.

The present disclosure relates to the subject matter contained in Japanese patent application No. Hei. 10-230372 (filed on Aug. 17, 1998), which is expressly incorporated herein by reference in its entirety.

BRIEF DESCRIPTION OF THE DRAWINGS

In the accompanying drawings:

FIG. 16 is a longitudinal section of the distal end portion of an endoscopic treatment tool according to the ninth embodiment of the invention;

FIG. 17 FIGS. 17(A), 17(B), and 17(C) show shows in perspective view three examples of the shape of the opening made near the distal end of the flexible sheath in the ninth embodiment of the invention.

DESCRIPTION OF THE PREFERRED EMBODIMENT

Several embodiments of the present invention are described below with reference to the accompanying drawings.

Figure 1:
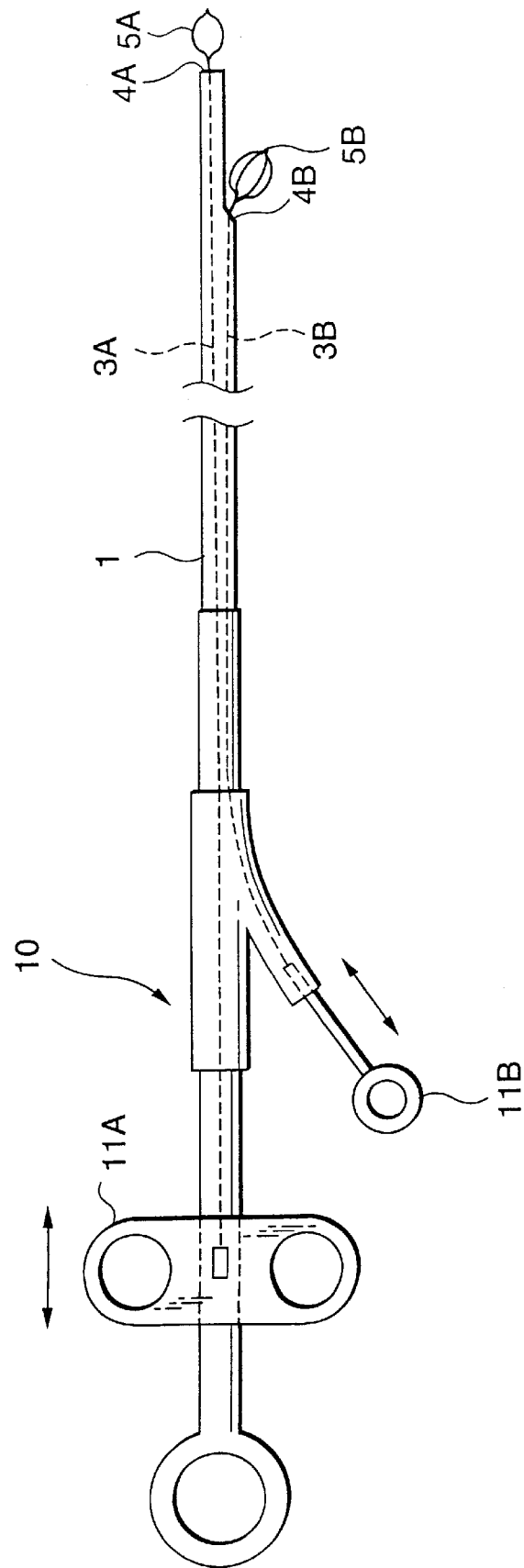
FIG. 1 is a side view showing the general layout of an endoscopic treatment tool according to the first embodiment of he invention.

FIG. 1 shows the general layout of an endoscopic treatment tool. Indicated by 1 is an electrically insulating, flexible sheath that is to be passed into or out of a treatment insertion channel in an endoscope (not shown). The sheath may typically be in the form of a poly(tetrafluoroethylene) tube, with a control section 10 being coupled to the basal end (the proximal end closer to the operator).

Figure 2:
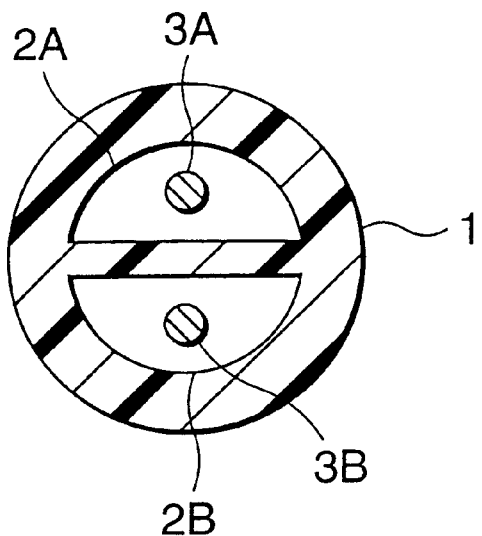
FIG. 2 is a section of the flexible sheath in the first embodiment of the invention which is taken across a plane perpendicular to its longitudinal axis.
Figure 3:
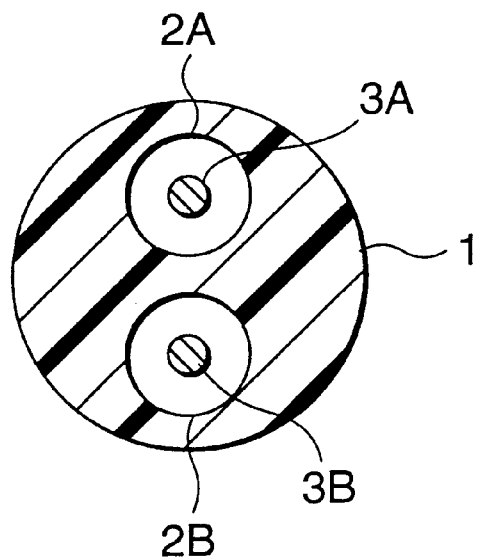
FIG. 3 is a section of a modification of the flexible sheath in the first embodiment of the invention which is taken across a plane perpendicular to its longitudinal axis.

As shown in FIG. 2 (a section taken across a plane perpendicular to the longitudinal axis), the flexible sheath 1 has two passages 2A and 2B formed through the entire length parallel to the longitudinal axis. In FIG. 2, the two passages 2A and 2B are shown to have a semicircular cross section but they may be circular as shown in FIG. 3 or may assume other shapes.

Figure 4:
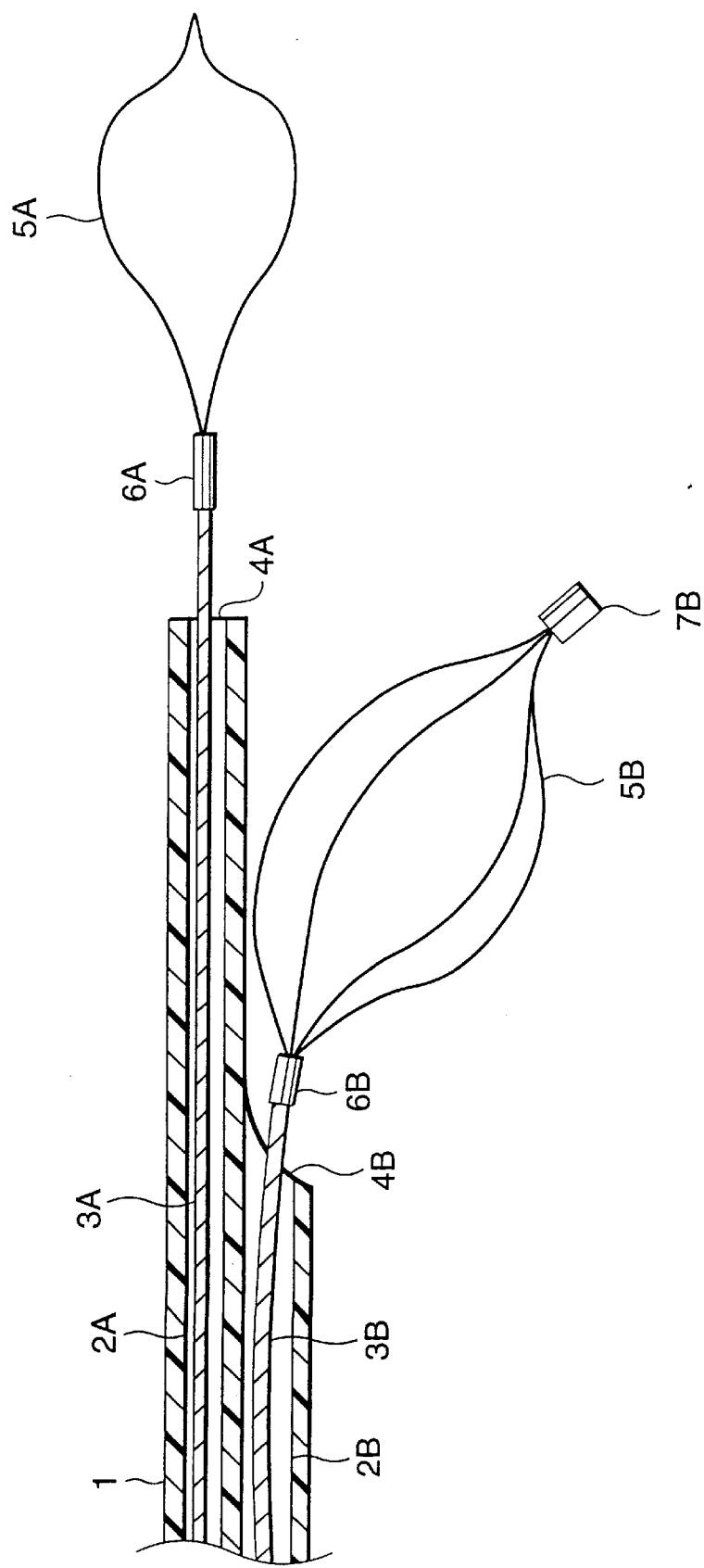
FIG. 4 is a longitudinal section of the distal end portion of the endoscopic treatment tool according to the first embodiment of the invention.

FIG. 4 shows the distal end portion of the flexible sheath 1. As shown, the first passage 2A is open in the surface of the distal end of the flexible sheath 1. The opening of the first passage at the distal end is indicated by 4A in FIG. 1. The second passage 2B is open near the distal end of the flexible sheath 1 (typically in a position about 5 to 50 mm distant from the distal end). The opening of the second passage near the distal end is indicated by 4B in FIG. 1.

Beyond and in the area more distal the opening 4B near the distal end of the flexible sheath 1, the second passage 2B is cut off so that the outer shape of the flexible sheath 1 is sized to be thinner by an amount corresponding to the elimination of the second channel 2B.

Two manipulating wires 3A and 3B are independently passed through the first and second passages 2A and 2B, one wire per passage, such that they can be moved back and forth along the longitudinal axis. The manipulating wires 3A and 3B have treating members 5A and 5B coupled to the respective distal ends via coupling tubes 6A and 6B.

The treating member coupled to the distal end of the first manipulating wire 3A is a high-frequency snare loop 5A for severing a polyp by cauterization with a high-frequency current as it is tightened with the loop. Typically, the high-frequency snare loop 5A is formed of a stainless steel wire or other conductive, elastic wire that is bent in a loop shape. In order to pass a high-frequency current through the snare loop 5A, both the first manipulating wire 3A and the first coupling tube 6A are also formed of a conductive metal.

The treating member coupled to the distal end of the second manipulating wire 3B is a foreign matter retaining member of basket type 5B for retaining and retrieving severed polyps. Typically, the member 5B is formed of three or four elastic wires such as stainless steel wires that are bent in a basket shape.

The distal end portion of the foreign matter retaining member 5B is passed through a tip 7B so that the wires are bundled together. The tip 7B may be sufficiently thick that it will not be pulled into the second passage 2B; alternatively, it may be thin enough to be pulled into the second passage 2B.

As shown in FIG. 1, the control section 10 is fitted with two sliders, the first slider 11A for causing the first manipulating wire 3A to move back and forth along the longitudinal axis and the second slider 11B for causing the second manipulating wire 3B to move back and forth along the longitudinal axis.

When the first slider 11A is pushed or pulled so that the first manipulating wire 3A advances or retracts accordingly, the high-frequency snare loop 5A ejects from or reenter the first passage 2A via the opening 4A at the distal end of the flexible sheath 1 which serves as an access hole. Outside the flexible sheath 1, the high-frequency snare loop 5A expands under its own elasticity; when it is pulled into the first passage 2A, the loop deforms elastically to contract.

When the second slider 11B is pushed or pulled so that the second manipulating wire 3B advances or retracts accordingly, the foreign matter retaining member 5B ejects from or reenter the second passage 2B via the opening 4B near the distal end of the flexible sheath 1 which serves as an access hole. Outside the flexible sheath 1, the member 5B expands under its own elasticity; when it is pulled into the second passage 2B, the member deforms elastically to contract.

Figure 5:
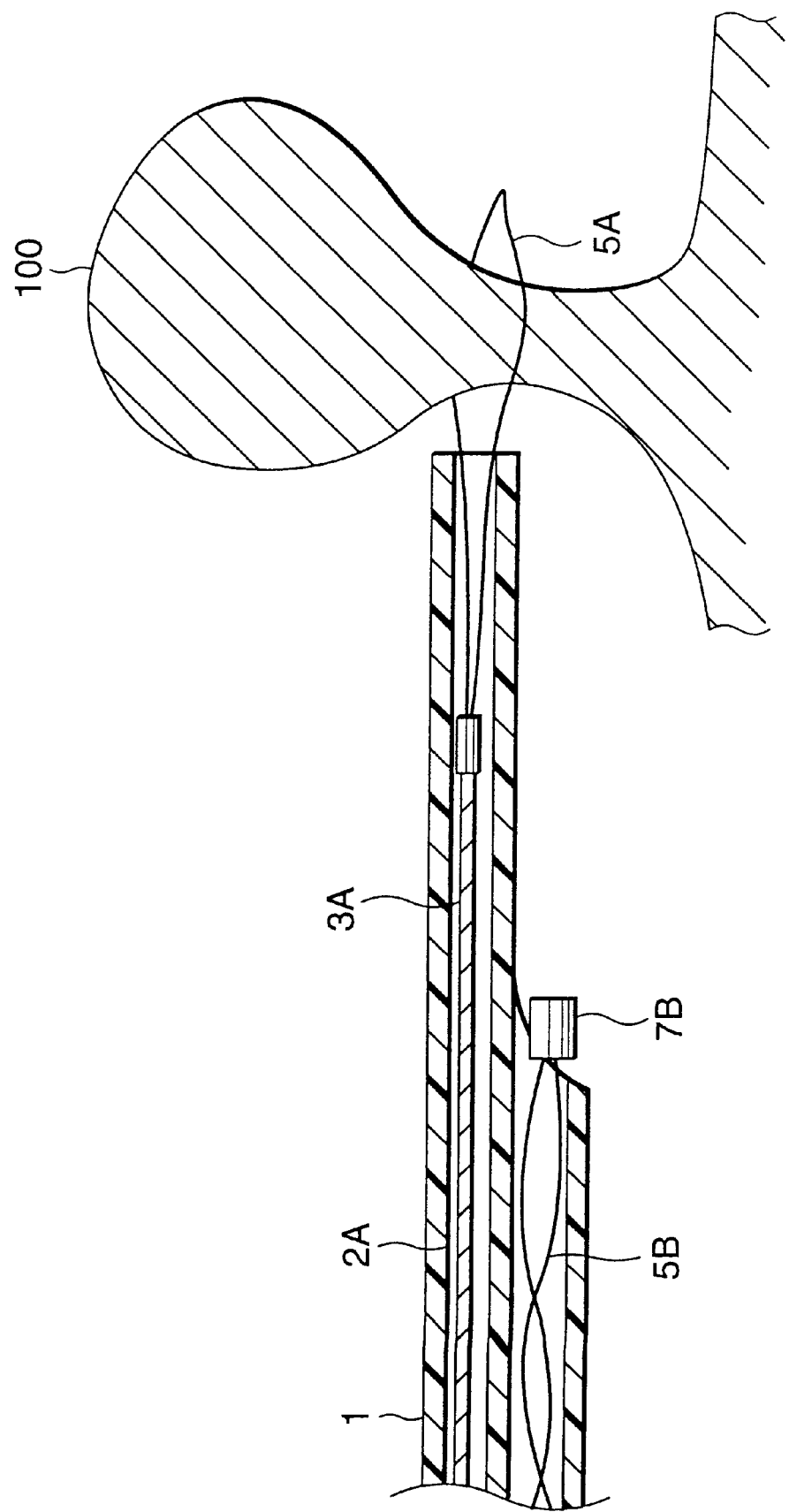
FIG. 5 is a longitudinal section of the distal end portion of the endoscopic treatment tool according to the first embodiment of the invention as it is used in practice.

The endoscopic treatment tool in the embodiment under discussion is used in the following manner. First, the flexible sheath 1 is passed through a treatment tool insertion channel in an endoscope. Then, as shown in FIG. 5, a polyp 100 is encircled and tightened at the base with the high-frequency snare loop 5A, to which high-frequency current is applied to remove the polyp 100.

The removed polyp 100 is captured and retained in the foreign matter retaining member 5B. Since the member 5B is lateral to the flexible sheath 1, it does not interfere with the action of the high-frequency snare loop 5A in removing a second polyp. As a result, the second polyp can be removed and retained without the need to withdraw the flexible sheath 1 from the treatment tool insertion channel in an endoscope.

Figure 6:
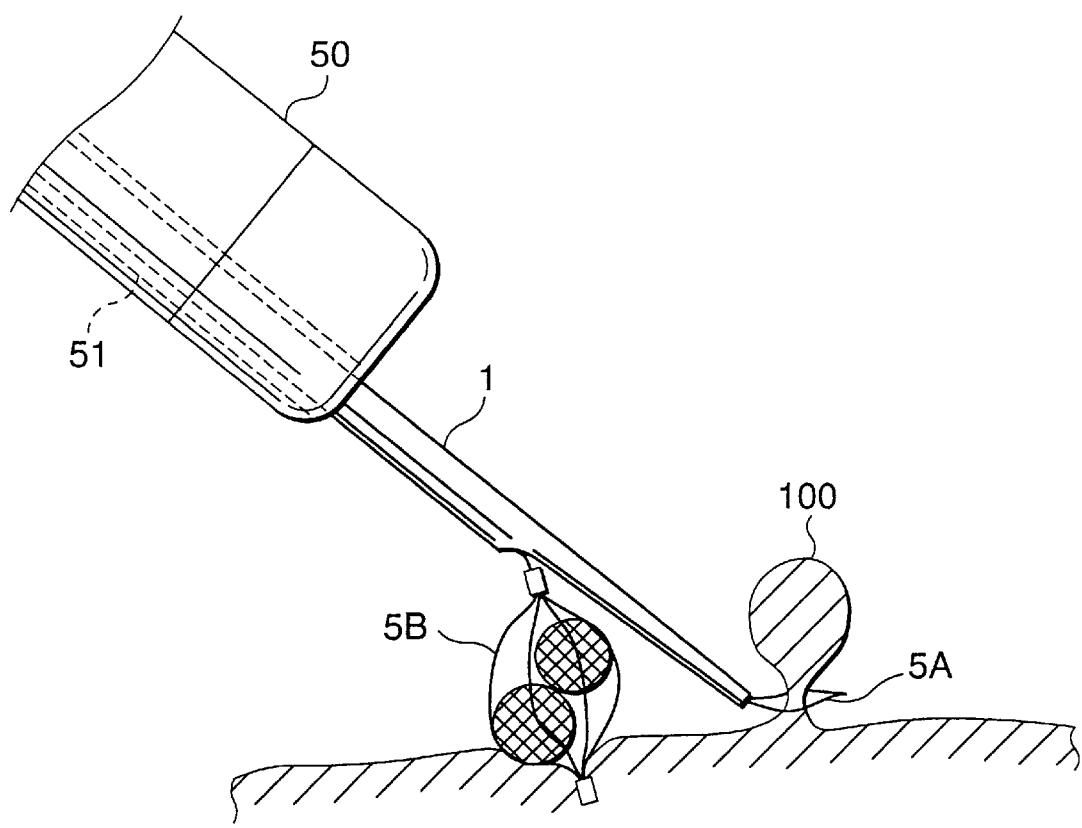
FIG. 6 is a side view of the distal end portion of the endoscopic treatment tool according to the first embodiment of the invention as it is used in practice.

FIG. 6 shows the situation more clearly; the flexible sheath 1 is not withdrawn out of the treatment tool insertion channel 51 in the endoscope 50 and yet the next polyp 100 is being removed with the high-frequency snare loop 5A with the already removed polyps retained in the member 5B. In this manner, a multiple of polyps can be removed and retained in succession.

Figure 7:
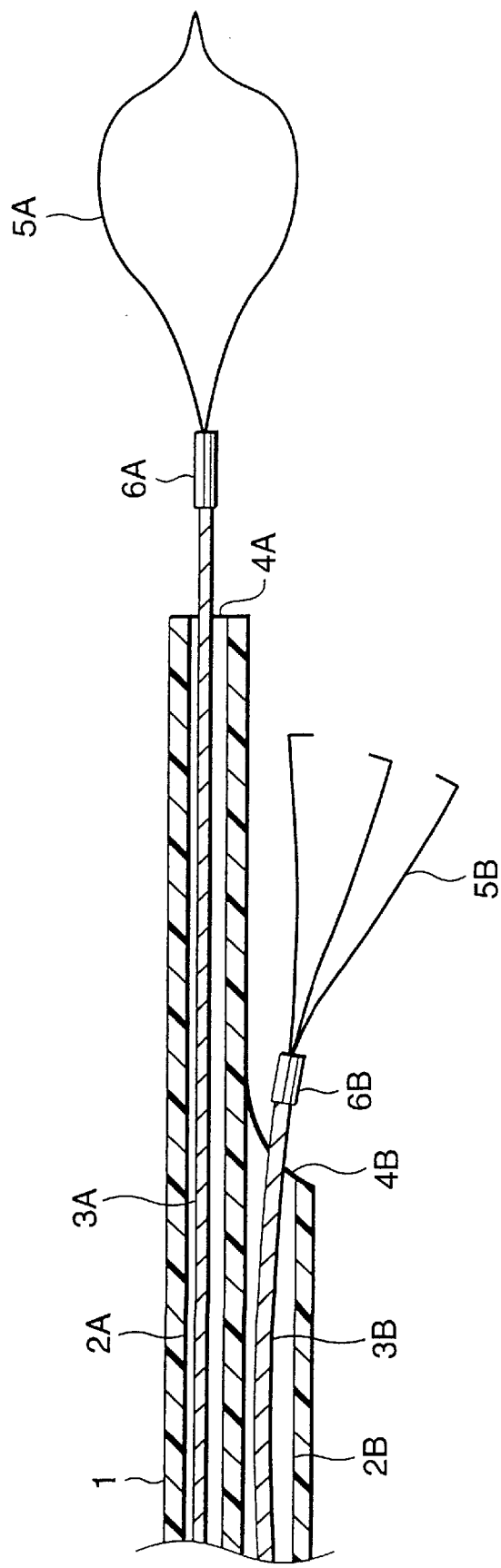
FIG. 7 is a longitudinal section of the distal end portion of an endoscopic treatment tool according to the second embodiment of the invention.
Figure 8:
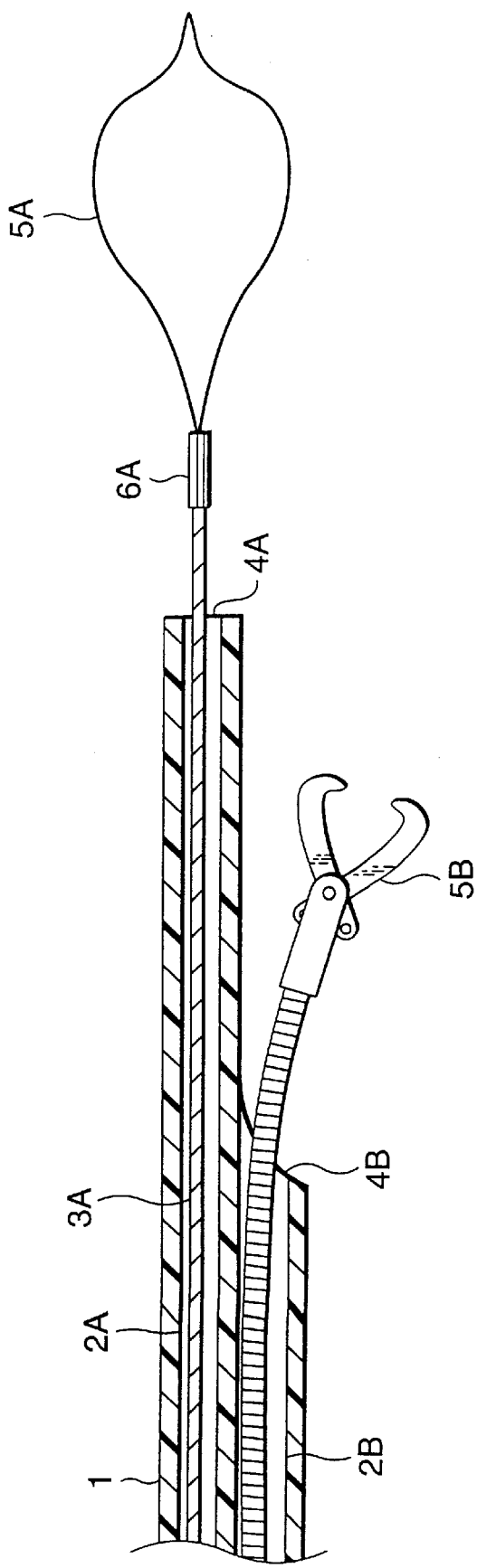
FIG. 8 is a longitudinal section of the distal end portion of an endoscopic treatment tool according to the third embodiment of the invention.
Figure 9:
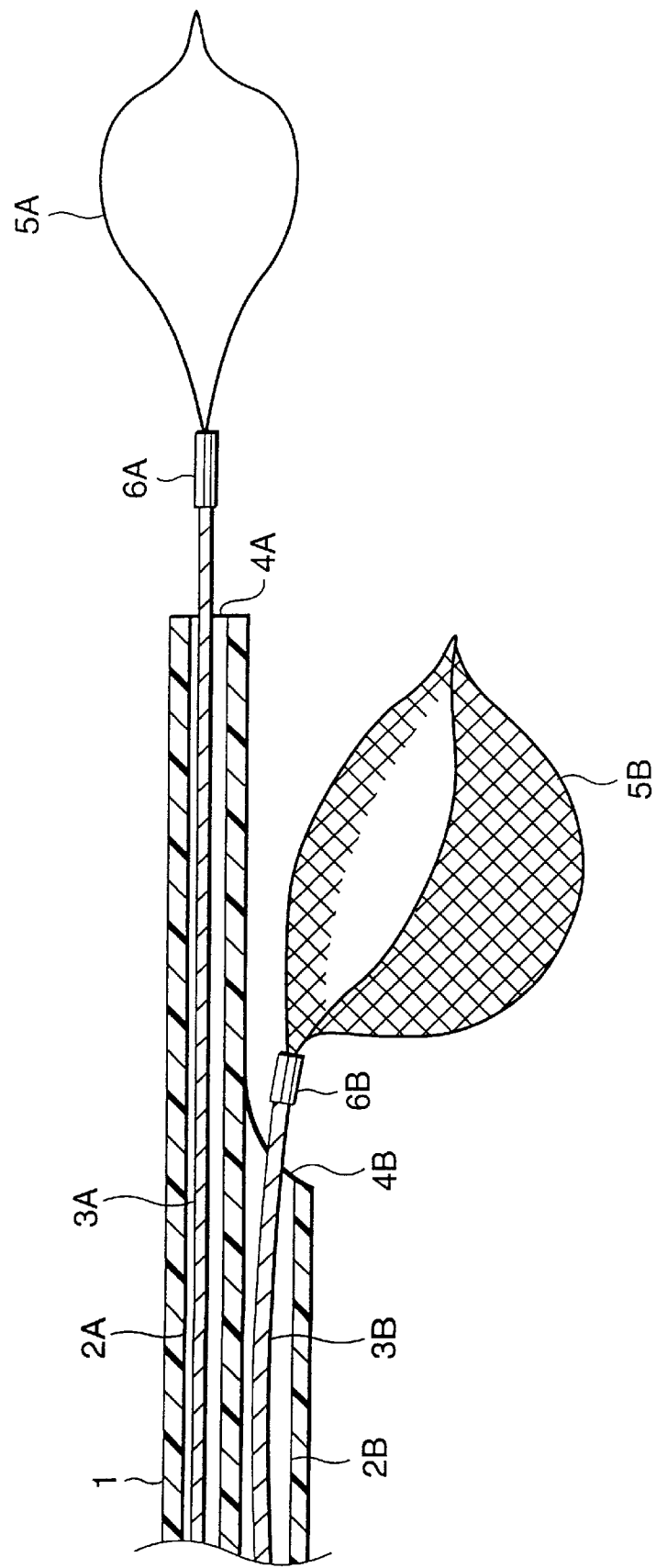
FIG. 9 is a longitudinal section of the distal end portion of an endoscopic treatment tool according to the fourth embodiment of the invention.

It should be noted here that the foreign matter retaining member 5B that is pushed out and pulled via the opening 4B near the distal end of the flexible sheath 1 need not be of a basket type but may assume various other shapes including the ones shown in FIGS. 7, 8 and 9. FIG. 7 shows the second embodiment of the invention, in which a plurality of claw members are adapted to open and close under their own elasticity; FIG. 8 shows the third embodiment, in which a pair of beak-shaped jaws are adapted to open and close with a link mechanism; and FIG. 9 shows the fourth embodiment, in which the foreign matter retaining member 5B is shaped like a butterfly net.

Figure 10:
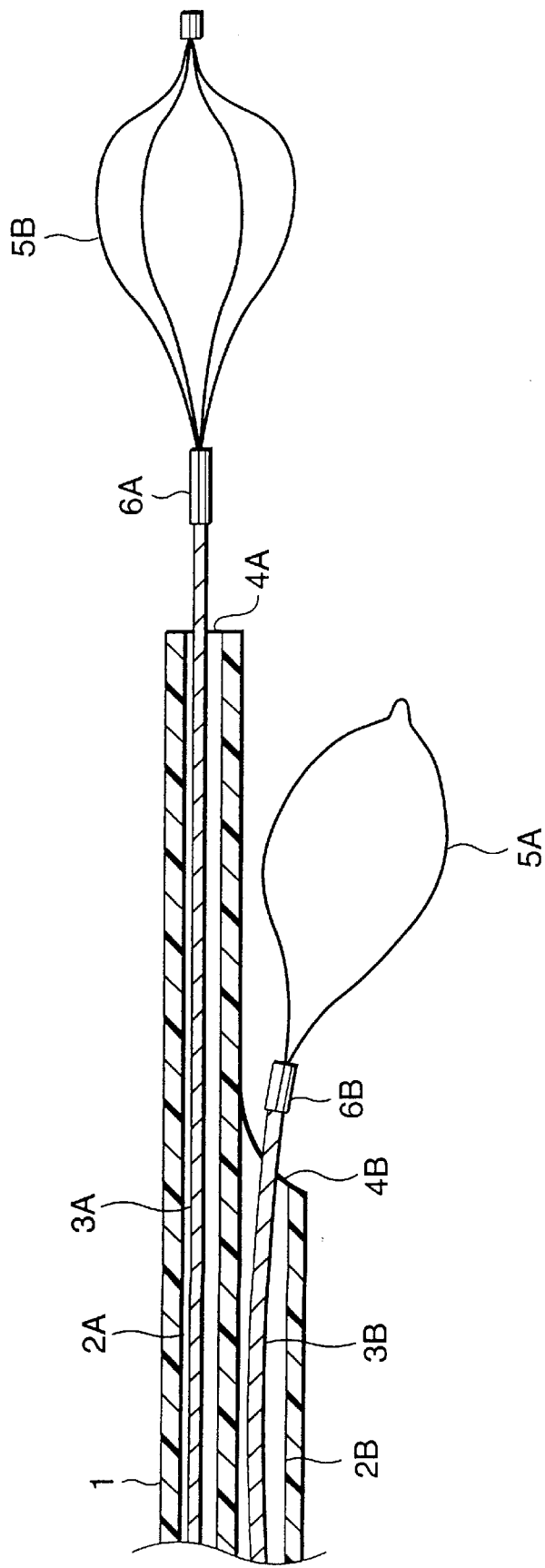
FIG. 10 is a longitudinal section of the distal end portion of an endoscopic treatment tool according to the fifth embodiment of the invention.

If desired, the positions of the high-frequency snare loop 5A and the foreign matter retaining member 5B may be reversed and this is the fifth embodiment of the invention which is shown in FIG. 10; the foreign matter retaining member 5B is pushed out and pulled via the opening 4A at the distal end of the flexible sheath 1 and the high-frequency snare loop 5A is pushed out and pulled via the opening 4B near the distal end of the flexible sheath 1.

Figure 11:
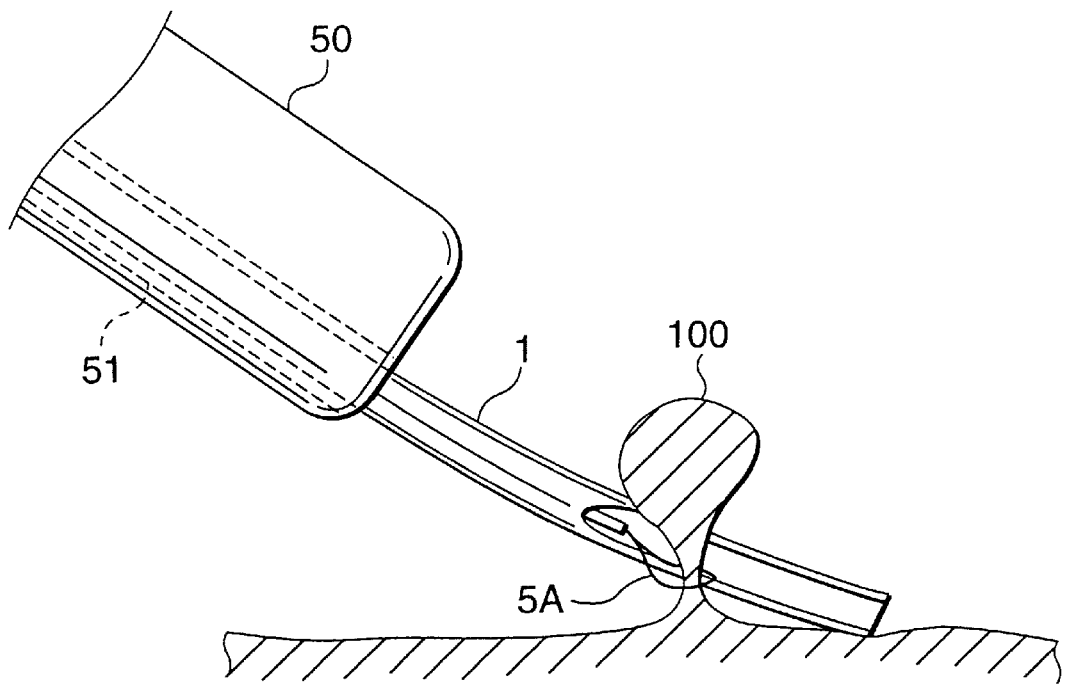
FIG. 11 is a side view of the distal end portion of the endoscopic treatment tool according to the fifth embodiment of the invention as it is used in practice.

The advantage of this alternative arrangement is clear from FIG. 11 and the distal end of the flexible sheath 1 is pressed against the surface polyp 100 of a mucous membrane so that it maintains a fixed relative position with the polyp 100 while the latter is encircled and tightened with the high-frequency snare loop 5A.

Figure 12:
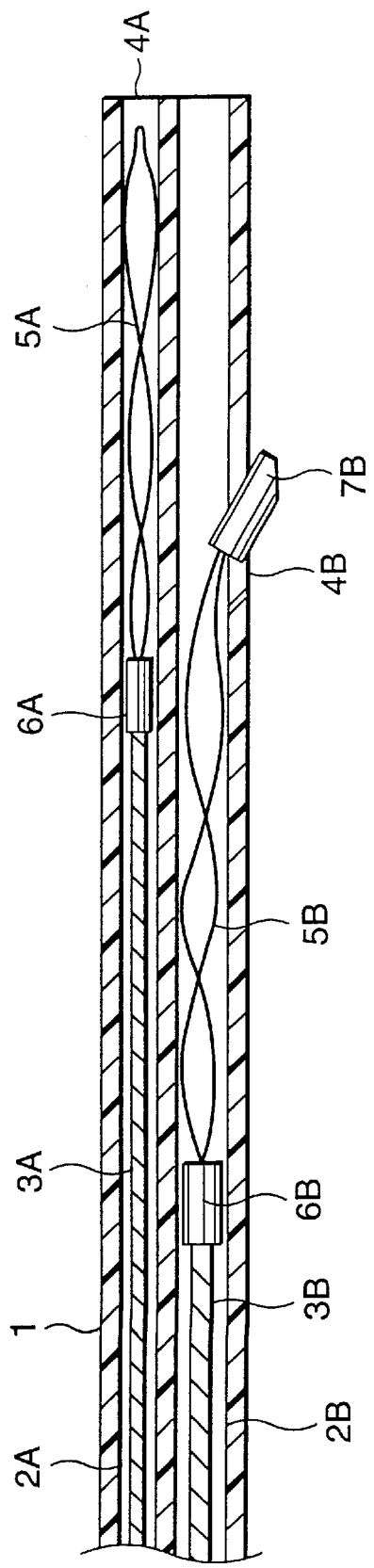
FIG. 12 is a longitudinal section of the distal end portion of an endoscopic treatment tool according to the sixth embodiment of the invention.

FIG. 12 shows the distal end portion of an endoscopic treatment tool according to the sixth embodiment of the invention. The opening 4B near the distal end of the flexible sheath 1 is formed in its sidewall and its outer shape has a uniform thickness up to the distal end.

Figure 13:
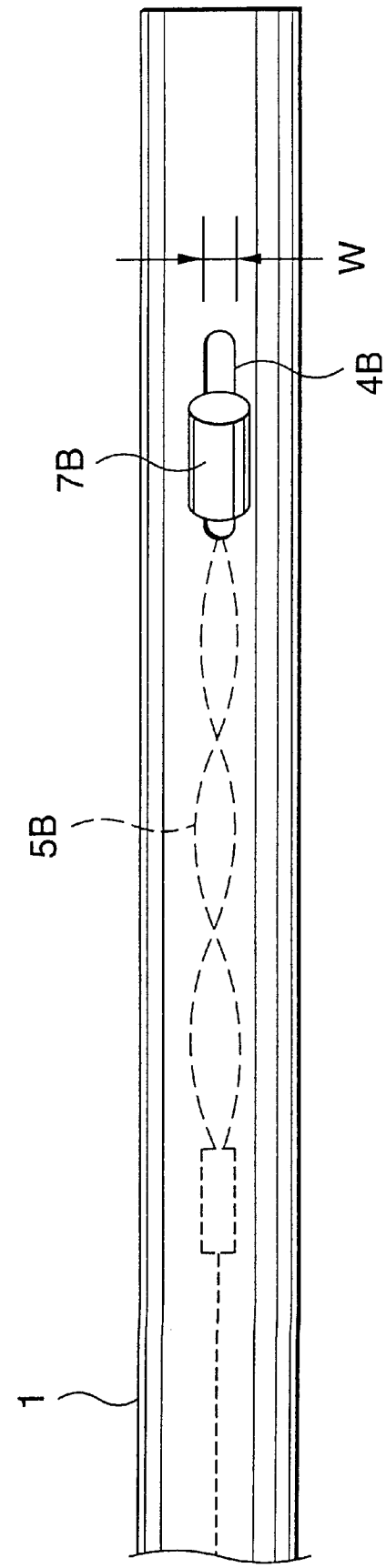
FIG. 13 is a bottom view of the distal end portion of the endoscopic treatment tool according to the sixth embodiment of the invention.

FIG. 13 is a bottom view of the flexible sheath 1 in the sixth embodiment. As shown, the opening 4B which is formed near the distal end of the flexible sheath 1 as an elongated slot parallel to the longitudinal axis of the sheath has a width W which is adapted to be smaller than the diameter of the tip 7B so that the latter will not be pulled into the second passage 2B.

Figure 14:
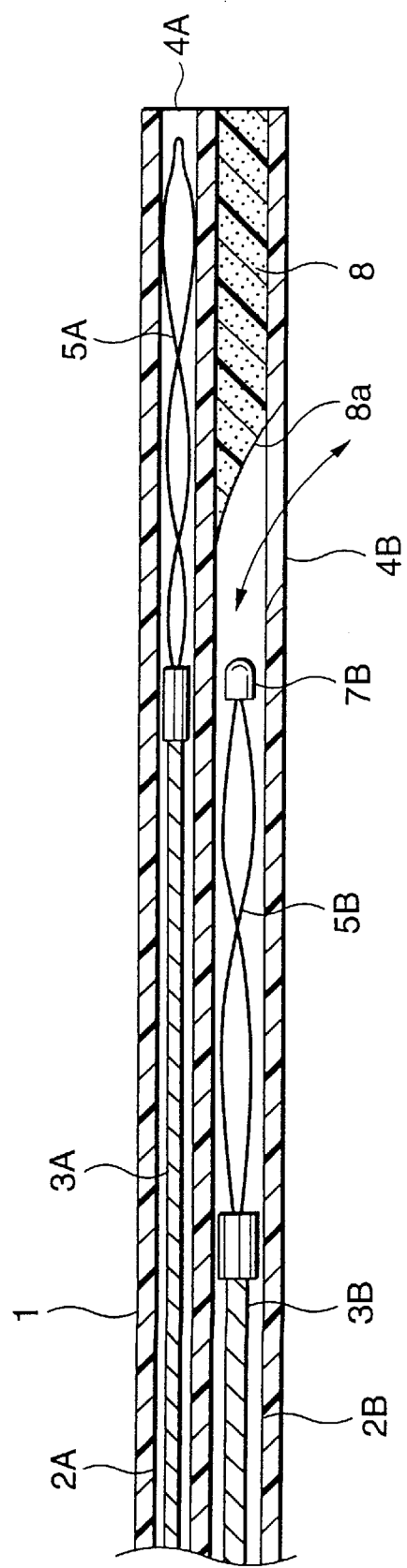
FIG. 14 is a longitudinal section of the distal end portion of an endoscopic treatment tool according to the seventh embodiment of the invention.

FIG. 14 shows the distal end portion of an endoscopic treatment tool according to the seventh embodiment of the invention. As shown, the seventh embodiment is the same as the sixth embodiment, except that the flexible sheath 1 is provided with a soft filling such as silicon rubber in that portion of the second passage 2B which is more distal than the opening 4B near the distal end.

The filling indicated by 8 in FIG. 14 forms a slope 8a by which the inner surface of the second passage 2B which is closer to the basal end than the opening 4B near the distal end is smoothly connected to the opening 4B. This design has the advantage that even if the tip 7B is small enough to be pulled into the second passage 2B via the opening 4B, one only needs to let the second manipulating wire 3B advance or retract so that the foreign matter retaining member 5B is pushed out or pulled via the opening 4B.

Figure 15:
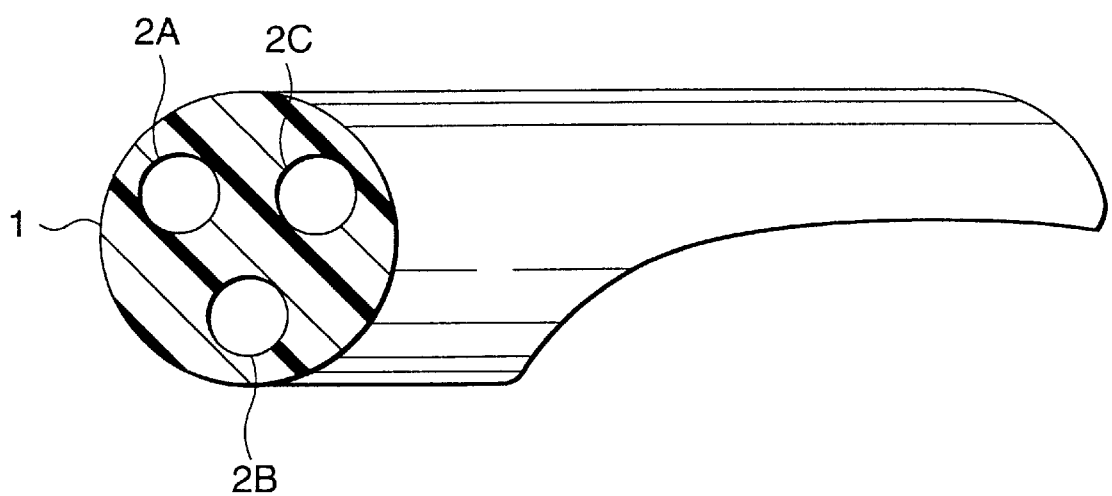
FIG. 15 is a perspective section of a flexible sheath in an endoscopic treatment tool according to the eighth embodiment of the invention.

In each of the first to seventh embodiments described above, the flexible sheath 1 is a so-called "multi-lumen tube" having the two passage 2A and 2B formed therein. If desired, another passage such as one for feeding water to wash blood off may be additionally provided as shown in FIG. 15. This is the eighth embodiment of the invention.

FIG. 16 shows the distal end portion of an endoscopic treatment tool according to the ninth embodiment of the invention. As shown, the flexible sheath 1 is a single-orifice, insulating, flexible tube and two manipulating wires, the first wire 3A having the high-frequency snare loop 5A coupled to the distal end and the second wire 3B having the foreign matter retaining member 5B coupled to the distal end, are collectively passed into a single passage 2.

An opening 4B is formed in the sidewall of the flexible sheath 1 in a position near its distal end so that the foreign matter retaining member 5B can be pushed out and pulled into the flexible sheath 1 via the opening 4B. On the other hand, the high-frequency snare loop 5A is pushed out and pulled via the opening 4A at the distal end.

Hence, the endoscopic treatment tool according to the ninth embodiment can be used in the same manner as shown in FIG. 6. Note that at least one of the two manipulating wires 3A and 3B is provided with an electrically insulating coat to ensure that there is no leakage of a high-frequency current to the foreign matter retaining member 5B.

Figure 17A:
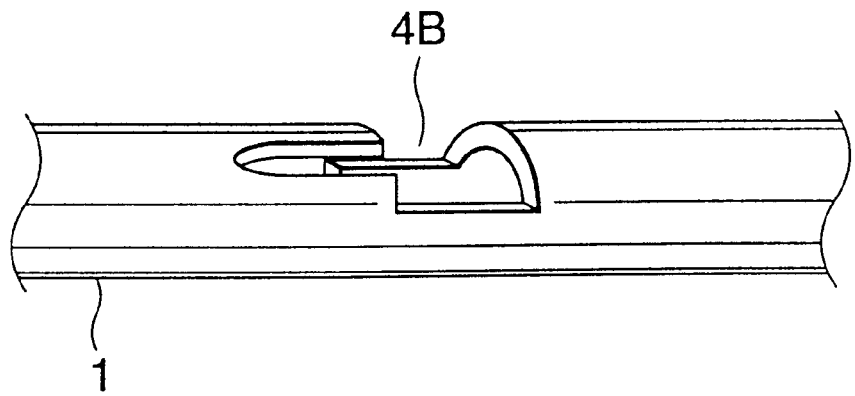
Figure 17B:
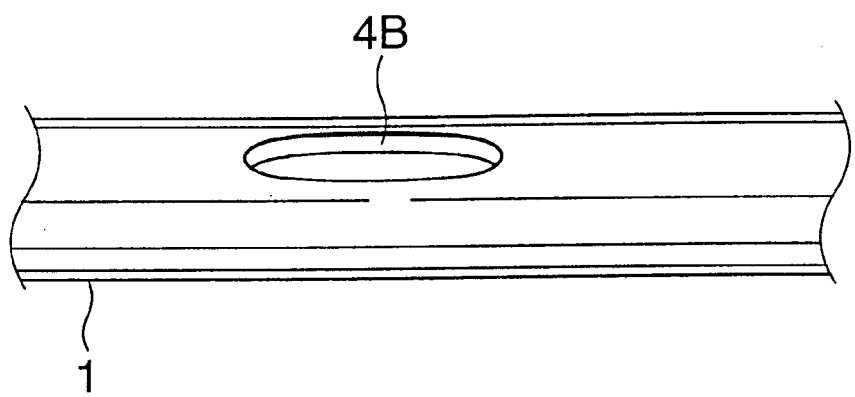
Figure 17C:
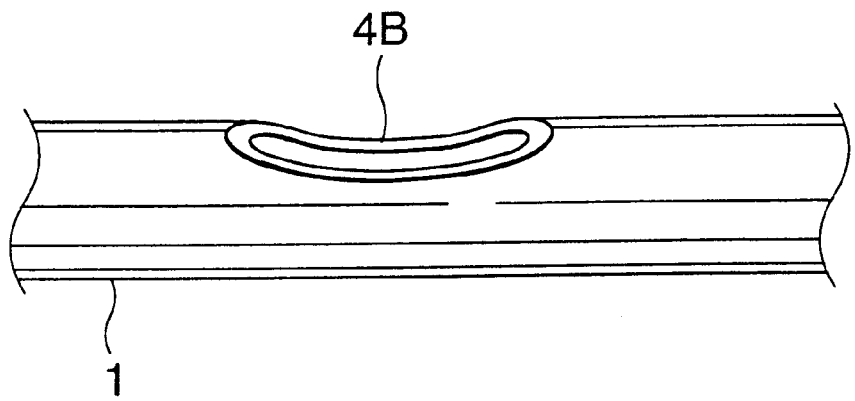

The opening 4B near the distal end of the flexible sheath 1 has such a shape and a size that it does not permit the passage of the tip 7B that bundles the wires in the distal end of the foreign matter retaining member 5B. As long as this requirement is met, the opening 4B may assume any shape, some of which are shown in FIGS. 17A, 17B and 17C.

Figure 18:
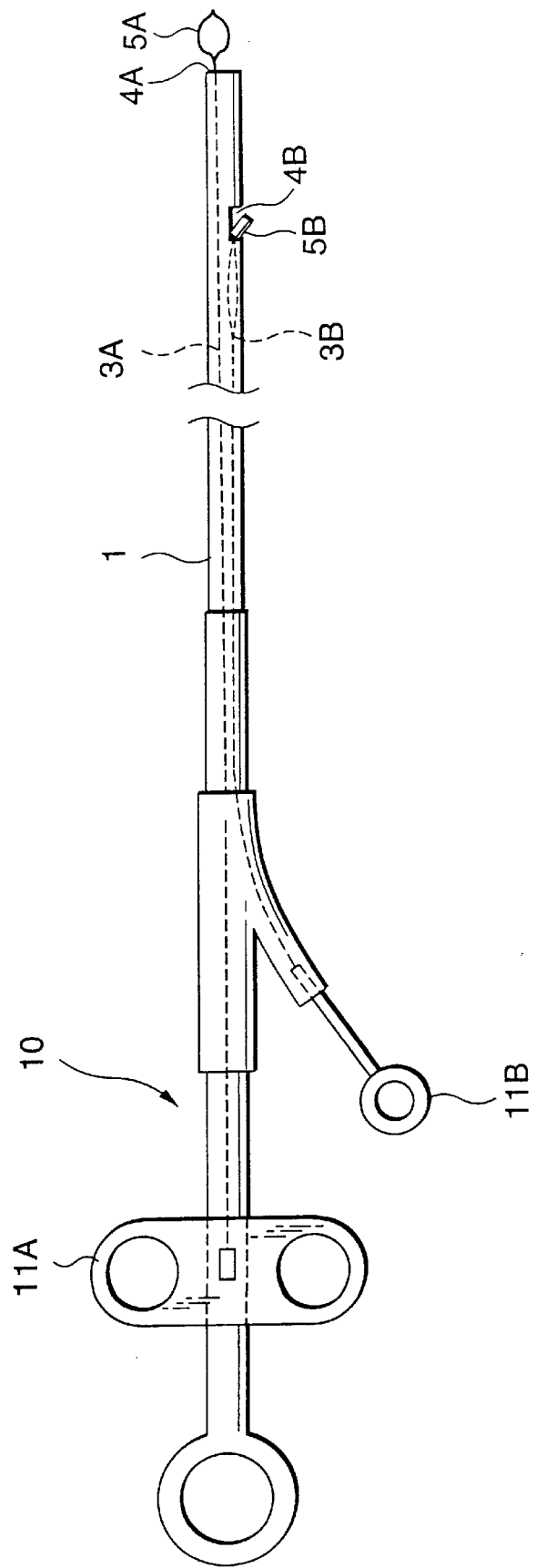
FIG. 18 is a side view showing the general layout of the endoscopic treatment tool according to the ninth embodiment of the invention.

FIG. 18 shows the general layout of the endoscopic treatment tool according to the above-described ninth embodiment of the invention, in which the control section 10 may be of the same type as used in the first embodiment.

According to the present invention, one of the treating members coupled to the distal end of manipulating wires is adapted to have access to a flexible sheath via the opening at its distal end of the sheath whereas the other treating members are adapted to have access to the flexible sheath via the opening near its distal end. This arrangement allows two treating members such as a high-frequency snare loop and a foreign matter retaining member to be pushed out and pulled into the flexible sheath without interfering with each other. As a result, the treatment tool of the invention can repeat a plurality of treatments including the removal and retrieval of polyps without being withdrawn from an endoscope, thereby achieving a marked reduction in the time required to complete the intended treatments.

What is claimed is:

1. An endoscopic treatment tool comprising:
    a flexible sheath that is to be passed into or out of a treatment tool insertion channel in an endoscope and which has openings respectively formed at and near a distal end of the flexible sheath to communicate with an interior of said flexible sheath; and
    at least two manipulating wires that have treating members coupled to distal ends of said at least two manipulating wires, respectively, and which are passed through said flexible sheath such that they can be moved back and forth along the longitudinal axis independently of each other, one of said treating members being provided to have access to said flexible sheath via said opening at its distal end and the other of said treating members being provided to have access to said flexible sheath via said opening near its distal end.

2. The endoscopic treatment tool according to claim 1, wherein the treating member which has access to said flexible sheath via the opening at its distal end is a high-frequency snare loop and the treating member which has access to said flexible sheath via the opening near said distal end is a foreign matter retaining member.

3. The endoscopic treatment tool according to claim 1, wherein the treating member which has access to said flexible sheath via the opening at its distal end is a foreign matter retaining member and the treating member which has access to said flexible sheath via the opening near said distal end is a high-frequency snare loop.

4. The endoscopic treatment tool according to claim 1, wherein at least two passages through which said at least two manipulating wires are respectively passed independently of each other are formed through said flexible sheath along the longitudinal axis.

5. The endoscopic treatment tool according to claim 4, wherein a passage communicating with said opening near the distal end of said flexible sheath terminates at said opening near the distal end of said flexible sheath, and a portion of the flexible sheath which is more distal than said opening near the distal end is reduced in outer dimension in comparison with a portion of the flexible sheath which is more proximal than said opening near the distal end.

6. The endoscopic treatment tool according to claim 1, wherein said opening near the distal end of said flexible sheath is formed in a sidewall of said flexible sheath.

7. The endoscopic treatment tool according to claim 6, herein at least two passages through which said at least two manipulating wires are respectively passed independently of each other are formed through said flexible sheath along the longitudinal axis, and a soft filling is provided in a portion of the passage communicating with said opening near the distal end which is more distal than said opening near the distal end.

8. The endoscopic treatment tool according to claim 7, wherein said filling forms a slope by which an inner surface of a portion of said passage which is closer to the proximal end than said opening near the distal end is connected smoothly to said opening.

9. The endoscopic treatment tool according to claim 1, wherein said at least two manipulating wires are collectively passed through a single passage formed through said flexible sheath along the longitudinal axis.

10. The endoscopic treatment tool according to claim 9, wherein at least one of said at least two manipulating wires is provided with an electrically insulating coat.

11. The endoscopic treatment tool according to any one of claim 1, wherein a fluid passage is formed through said flexible sheath along the longitudinal axis separately from a passage or passages through which said at least two manipulating wires are to be passed.

12. The endoscopic treatment tool according to claim 1, wherein a tip is provided at a distal end of the treating member that has access to said flexible sheath via the opening near the distal end, said tip being of such a shape and a size that it is incapable of passing through said opening near the distal end.

13. An endoscopic treatment tool adapted to be passed into or out of a treatment tool insertion channel in an endoscope, said treatment tool comprising:

an elongated flexible sheath defining a longitudinal axis and having first and second openings located offset from each other along said longitudinal axis;

a snare loop protruded from said first opening;

a foreign matter retaining member protruded from said second opening;

a control section provided to said flexible sheath and located opposite from said first and second openings along said longitudinal axis; and first and second manipulating wires operatively connecting said snare loop and said foreign matter retaining member to said control section.

14. The endoscopic treatment tool according to claim 13, wherein said first opening is distanced from said second opening about 5 to 50 mm along said longitudinal axis.

15. The endoscopic treatment tool according to claim 14, wherein one of said first and second openings is located at an axial terminus of said flexible sheath.

16. The endoscopic treatment tool according to claim 15, wherein said flexible sheath is in the form of a multi-lumen tube.

17. The endoscopic treatment tool according to claim 15, wherein said flexible sheath has a single passage communicating with both said first and second openings and accommodating both said first and second manipulating wires therein.

\* \* \* \* \*